000

(12) United States Patent
Colby

(10) Patent No.: US 9,901,366 B2
(45) Date of Patent: Feb. 27, 2018

(54) SYSTEMS AND METHODS FOR ENHANCING THE VISIBILITY OF MEDICAL ITEMS

(71) Applicant: Lawrence A. Colby, Ashburn, VA (US)

(72) Inventor: Lawrence A. Colby, Ashburn, VA (US)

( * ) Notice: Subject to any disclaimer, the term of this patent is extended or adjusted under 35 U.S.C. 154(b) by 194 days.

(21) Appl. No.: 14/309,412

(22) Filed: Jun. 19, 2014

(65) Prior Publication Data

US 2015/0032070 A1    Jan. 29, 2015

Related U.S. Application Data

(60) Provisional application No. 61/859,183, filed on Jul. 27, 2013, provisional application No. 61/969,258, filed on Mar. 23, 2014.

(51) Int. Cl.
*A61F 13/44* (2006.01)
*A61B 17/3211* (2006.01)
(Continued)

(52) U.S. Cl.
CPC .......... *A61B 17/3211* (2013.01); *A61B 90/94* (2016.02); *A61F 13/44* (2013.01); *A61B 2090/0804* (2016.02)

(58) Field of Classification Search
CPC ... A61F 13/36; A61F 13/44; A61B 2090/0804
See application file for complete search history.

(56) References Cited

U.S. PATENT DOCUMENTS

| 1,435,110 A | 11/1922 | Efford |
| 1,818,761 A | 8/1931 | Sendler |

(Continued)

FOREIGN PATENT DOCUMENTS

| CN | 103124526 A | 5/2013 |
| WO | WO 2004/082466 | 9/2004 |
| WO | WO 2004/094495 | 11/2004 |

OTHER PUBLICATIONS

International Search Report and Written Opinion in corresponding Int'l Application No. PCT/US2014/043243, dated Oct. 16, 2014 (10 pages).

*Primary Examiner* — Paula L. Craig
(74) *Attorney, Agent, or Firm* — Nixon Peabody LLP

(57) ABSTRACT

Systems and methods make medical items more visible during a medical procedure. An example medical item includes an absorbent material adapted to absorb fluid during a medical procedure, the absorbent material having an outer surface that reflects one or more first wavelengths of light to provide the absorbent material with one or more first colors. The medical item may include one or more enhancing materials disposed on at least one portion of the outer surface of the absorbent material, the one or more enhancing materials reflecting or emitting one or more second wavelengths to provide the enhancing materials with one or more second colors. Alternatively, an enhancing device is coupled to the absorbent material, the enhancing device reflecting or emitting one or more second wavelengths, the one or more second wavelengths being different from the one or more first wavelengths of the absorbent material.

16 Claims, 13 Drawing Sheets

(51) Int. Cl.
*A61B 90/94* (2016.01)
*A61B 90/00* (2016.01)

(56) References Cited

U.S. PATENT DOCUMENTS

| | | |
|---|---|---|
| 2,561,806 A | 7/1951 | Mailland |
| 2,987,193 A | 6/1961 | Pajor |
| 3,089,484 A * | 5/1963 | Hett .......................... A61B 1/07 |
| | | 385/107 |
| 3,097,649 A * | 7/1963 | Gray ....................... A61B 6/12 |
| | | 128/DIG. 14 |
| 3,133,538 A | 5/1964 | Pratt et al. |
| 3,698,393 A * | 10/1972 | Stone ....................... A61B 6/12 |
| | | 604/362 |
| 3,736,935 A | 6/1973 | Reimels |
| 3,749,237 A | 7/1973 | Dorton |
| 3,756,241 A * | 9/1973 | Patience ................... A61B 6/12 |
| | | 604/362 |
| 3,911,922 A | 10/1975 | Kliger |
| 3,941,132 A * | 3/1976 | Lenaghan ............. A61F 15/001 |
| | | 604/362 |
| 3,948,390 A * | 4/1976 | Ferreri .................... A61F 13/44 |
| | | 206/370 |
| 3,965,907 A | 6/1976 | Hardy et al. |
| 4,068,666 A | 1/1978 | Shiff |
| 4,205,680 A | 6/1980 | Marshall |
| 4,244,369 A | 1/1981 | McAvinn et al. |
| 4,295,537 A | 10/1981 | McAvinn et al. |
| 4,408,996 A * | 10/1983 | Baldwin ........... A61F 13/00008 |
| | | 128/849 |
| 4,428,488 A | 1/1984 | McAvinn et al. |
| 4,626,251 A | 12/1986 | Shen |
| 4,639,253 A | 1/1987 | Dyer et al. |
| 4,718,897 A | 1/1988 | Elves |
| 4,838,253 A * | 6/1989 | Brassington ...... A61F 13/00008 |
| | | 128/DIG. 21 |
| 4,917,694 A | 4/1990 | Jessup |
| 4,935,019 A | 6/1990 | Papp, Jr. |
| 4,938,901 A | 7/1990 | Groitzsch et al. |
| 4,983,173 A | 1/1991 | Patience et al. |
| 4,987,893 A * | 1/1991 | Salamone ................ A61L 15/26 |
| | | 128/DIG. 21 |
| 5,041,103 A | 8/1991 | Rupinskas |
| 5,045,080 A | 9/1991 | Dyer et al. |
| 5,112,325 A | 5/1992 | Zachry |
| 5,340,363 A * | 8/1994 | Fabo ................. A61F 13/00063 |
| | | 424/446 |
| 5,556,391 A * | 9/1996 | Cercone ................... A61F 13/36 |
| | | 602/46 |
| 5,582,301 A | 12/1996 | Josephson |
| 5,608,225 A * | 3/1997 | Kamimura ................ G06K 7/12 |
| | | 250/271 |
| 5,647,840 A * | 7/1997 | D'Amelio ........... A61B 1/00091 |
| | | 600/169 |
| 5,931,824 A * | 8/1999 | Stewart .................... A61F 13/44 |
| | | 604/358 |
| 5,955,776 A | 9/1999 | Ishikawa |
| 6,026,818 A | 2/2000 | Blair et al. |
| 6,070,747 A | 6/2000 | Shea |
| 6,196,398 B1 | 3/2001 | Lowe |
| 6,366,206 B1 | 4/2002 | Ishikawa et al. |
| 6,371,904 B1 | 4/2002 | Sirimanne et al. |
| 6,607,170 B1 | 8/2003 | Hoftman |
| 6,777,623 B2 | 8/2004 | Ballard |
| 7,297,834 B1 * | 11/2007 | Shapiro ................... A61F 13/44 |
| | | 604/356 |
| 7,303,798 B2 * | 12/2007 | Bavaro ................ A61B 5/1076 |
| | | 428/36.4 |
| 7,465,847 B2 | 12/2008 | Fabian |
| 8,544,660 B2 | 10/2013 | Foley |
| 2002/0021003 A1 * | 2/2002 | McGrew ................ B41M 3/144 |
| | | 283/93 |
| 2002/0029032 A1 * | 3/2002 | Arkin ...................... A61B 17/00 |
| | | 606/1 |
| 2003/0112624 A1 * | 6/2003 | Quittner ................... F21L 4/045 |
| | | 362/200 |
| 2003/0192722 A1 * | 10/2003 | Ballard ................ A61B 19/029 |
| | | 177/25.19 |
| 2004/0202625 A1 * | 10/2004 | Daniloff .................. A61L 31/14 |
| | | 424/63 |
| 2005/0038355 A1 | 2/2005 | Gellman et al. |
| 2005/0109347 A1 | 5/2005 | Falls, Jr. et al. |
| 2006/0089686 A1 * | 4/2006 | Streibich ............... A61N 5/0621 |
| | | 607/88 |
| 2006/0195054 A1 * | 8/2006 | Smith .................... A61F 13/023 |
| | | 602/54 |
| 2006/0282051 A1 * | 12/2006 | Reichheld .............. A61F 13/44 |
| | | 604/362 |
| 2007/0219516 A1 * | 9/2007 | Patel ....................... A61F 13/36 |
| | | 604/362 |
| 2007/0276308 A1 * | 11/2007 | Huey ................ A61F 13/00034 |
| | | 602/42 |
| 2008/0030303 A1 * | 2/2008 | Kobren .................... A61F 13/36 |
| | | 340/5.92 |
| 2008/0103510 A1 | 5/2008 | Taylor et al. |
| 2008/0138289 A1 * | 6/2008 | Goronkin ........... A61K 49/0063 |
| | | 424/9.4 |
| 2008/0312649 A1 | 12/2008 | Guerra et al. |
| 2009/0253967 A1 * | 10/2009 | Gill ..................... A61B 1/00059 |
| | | 600/249 |
| 2010/0267302 A1 * | 10/2010 | Kantner ................. A61L 15/585 |
| | | 442/71 |
| 2011/0163854 A1 * | 7/2011 | Hamelin ............. A61B 19/5244 |
| | | 340/10.1 |
| 2012/0034445 A1 * | 2/2012 | Ren ...................... A61B 19/088 |
| | | 428/221 |
| 2012/0071846 A1 * | 3/2012 | Shao ....................... A61F 13/36 |
| | | 604/362 |
| 2012/0095422 A1 * | 4/2012 | Morris .................. A61B 19/029 |
| | | 604/358 |
| 2012/0149992 A1 * | 6/2012 | Duggal ................... A61B 17/02 |
| | | 600/245 |
| 2012/0259302 A1 * | 10/2012 | Chaisumdet ........... A61F 13/44 |
| | | 604/367 |
| 2013/0053748 A1 * | 2/2013 | Cotton ............... A61F 13/00017 |
| | | 602/45 |
| 2013/0085434 A1 * | 4/2013 | Patel ................. A61F 13/00017 |
| | | 602/44 |
| 2013/0331657 A1 * | 12/2013 | Basson ................... A61B 90/30 |
| | | 600/249 |
| 2013/0344131 A1 * | 12/2013 | Lo ........................... A61L 15/18 |
| | | 424/447 |
| 2014/0107626 A1 * | 4/2014 | Byrne ................ A61B 19/0256 |
| | | 606/1 |
| 2014/0243770 A1 | 8/2014 | Stewart |
| 2014/0303606 A1 * | 10/2014 | Garner-Richards ... A61B 19/44 |
| | | 606/1 |
| 2015/0245955 A1 * | 9/2015 | Choudhury ............. A61F 13/36 |
| | | 206/440 |

\* cited by examiner

SYSTEMS AND METHODS FOR ENHANCING THE VISIBILITY OF MEDICAL ITEMS

CROSS REFERENCE TO RELATED APPLICATIONS

This application claims priority to U.S. Provisional Patent Application No. 61/859,183, filed Jul. 27, 2013, and U.S. Provisional Patent Application No. 61/969,258, filed Mar. 23, 2014, the contents of these applications being incorporated entirely herein by reference.

FIELD OF THE INVENTION

The present invention relates generally to medical items, and more particularly, to systems and methods for enhancing the visibility of medical items, such as surgical sponges, towels, and instruments, during a medical procedure, such as surgery.

BACKGROUND

Surgical procedures involve the use of many instruments and supplies. Despite existing protocols that are supposed to account for medical items before, during, and after each surgical procedure, surgical teams still lose track of medical items used during the procedure and leave medical items in the patient after the procedure is complete. Foreign objects that remain in the body after surgery may cause considerable post-operative pain, injure other anatomic structures, and/or cause infection or other foreign body reactions. Studies and government data indicate that a surgical instrument is inadvertently left in a patient between 4,500 and 6,000 times a year in the United States alone. Medical items are left behind in about 1 out of every 5,500 procedures, according to a 2014 study published by the Journal of the American College of Surgeons. Sponges, difficult to detect once saturated with blood, account for more than two-thirds of such incidents.

Due to the risks of such complications and associated financial/malpractice liabilities, most medical facilities must employ extensive positive control protocols to account for all medical items in the surgical environment before the patient is closed. These processes must account for all items that are used by the surgical team, including all surgical instruments, scalpels, knives, other hardware, containers, and absorbent items, such as sponges and towels. The location of each article that enters the surgical field must be positively controlled before, during, and after the medical procedure. In a typical surgical procedure, 20 to 300 medical items are used. In some surgical procedures, however, up to 600 medical items may be used, thus complicating the task of accounting for each medical items and increasing the risk of misplacing a medical item.

When the surgeon closes up the patient, the surgical team must positively identify the location of each item used during the surgical procedure. If a particular medical item cannot be accounted for, a search for the item is required, resulting in costly delays. Additional equipment, such as x-ray machines, may be required to x-ray the patient to determine if the medical item remains in the patient. Even when x-ray equipment is used, medical items can be missed in the x-ray photograph. If the medical item indeed remains in the patient, the patient must be reopened to retrieve the medical item. During this search, the patient must remain under anesthesia, extending beyond the planned duration for the medical procedure. The occasion for search and the need for x-ray equipment translate to extra costs to patients and insurance companies. Furthermore, such incidents require the submission of time-consuming incident reports by members of the surgical team and costly administrative review.

SUMMARY

Aspects of the present invention provide systems and methods to make medical items more visible in or around a surgical environment, which may include the patient, the area around the patient, the operating table, supply tables, the operating room, etc. The enhanced visibility makes it easier to account for medical items so that they are not misplaced or left in the patient. The systems and methods described herein reduce the time, expense, and risk associated with accounting for all medical items used in any type of medical procedure, such as surgery.

In one embodiment, a medical item includes an absorbent material, the absorbent material being adapted to absorb fluid during a medical procedure, the absorbent material having an outer surface that reflects one or more first wavelengths of light to provide the absorbent material one or more first colors. The medical item also includes one or more enhancing materials disposed on at least one portion of the outer surface of the absorbent material, the one or more enhancing materials reflecting or emitting one or more second wavelengths to provide the enhancing materials with one or more second colors, the one or more second wavelengths being different from the one or more first wavelengths of the absorbent material.

In some cases, the one or more enhancing materials may repel the fluid, such that the one or more enhancing materials continue to reflect or emit the one or more second colors when the one or more enhancing materials are exposed to the fluid. For example, the one or enhancing materials may include silicone, the silicone repelling the fluid. The silicone may be applied to the absorbent material in a pattern with openings through which the fluid can pass to be absorbed by the absorbent material.

In other cases, the one or more enhancing materials may include one or more strips that are applied to the outer surface of the absorbent material. The one or more strips may include a non-linear shape disposed along an edge of the absorbent material.

In yet other cases, the one or more enhancing materials may include a fluorescent, luminescent, photo-luminescent, or phosphorescent material. In further cases, the one or more enhancing materials include a reflective metallic material. In yet further cases, the one or more second wavelengths may be between approximately 485 nm to approximately 590 nm. In yet other cases, the one or more second wavelengths provide infrared light. In some cases, the one or more enhancing materials may include a mesh material that encloses the absorbent material, the mesh including openings that through which the fluid can pass to be absorbed by the absorbent material. In other cases, the one or more enhancing materials are applied to the absorbent material as a frame structure disposed along edges of the absorbent material.

In another embodiment, a medical item includes an absorbent material, the absorbent material being adapted to absorb fluid during a medical procedure, the absorbent material having an outer surface that reflects one or more first wavelengths of light to provide the absorbent material one or more first colors. The medical item includes an enhancing device coupled to the absorbent material, the enhancing device reflecting or emitting one or more second wavelengths, the one or more second wavelengths being different from the one or more first wavelengths of the absorbent material.

In some cases, the enhancing device includes a light device that includes a light source emitting the one or more second wavelengths. The light device may further include a liquid-tight housing including the light source, a battery, and a switch electrically coupled together in a circuit, the switch being selectively operable to deliver power from the battery to the light source and activate the light source to emit the one or more second wavelengths. The light device may emit pulsed light.

In other cases, the one or more second wavelengths are not in the visible spectrum and can only be seen through a camera or viewer. For example, the one or more second wavelengths may provide infrared light.

In yet other cases, the enhancing device may include a bead with a label uniquely assigned to the surgical item. In further cases, the enhancing device may include a tether that extends from the absorbent material.

Figure 1:
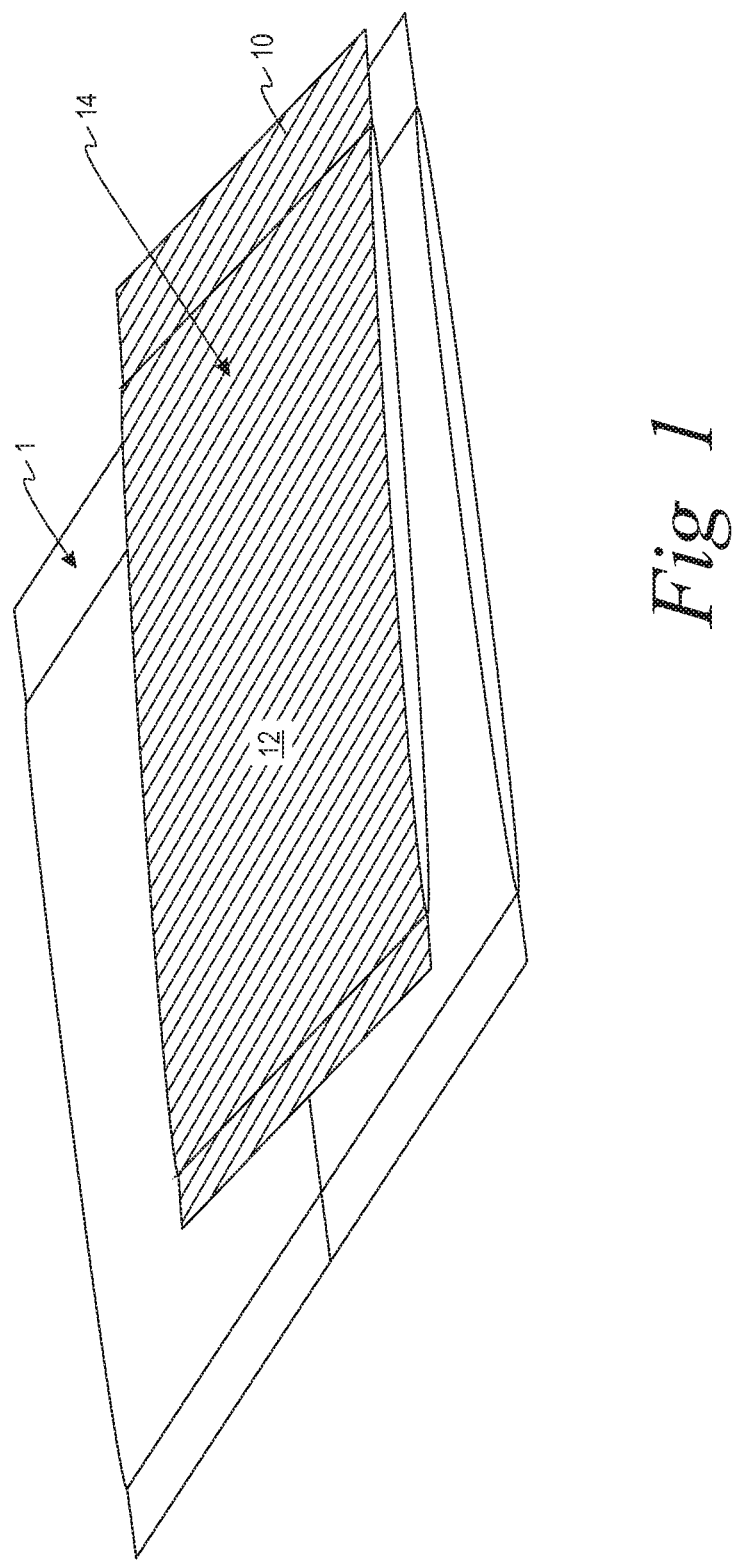
FIG. 1 illustrates an example sponge/towel with a highly visible colored surface, according to aspects of the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DETAILED DESCRIPTION

Aspects of the present invention provide systems and methods to make medical items more visible in or around a surgical environment, which may include the patient, the area around the patient, the operating table, supply tables, the operating room, etc. The enhanced visibility makes it easier to account for medical items so that they are not misplaced or left in the patient. The systems and methods described herein reduce the time, expense, and risk associated with accounting for all medical items used in any type of medical procedure, such as surgery.

In some embodiments, the medical items include highly visible colors (e.g., bright colors), patterns, labels (e.g., alphanumeric labels), images, shapes, structures, and/or materials (e.g., light-emitting material). Such highly visible features can be provided on any aspect of the medical items and are distinguishable from the other colors, shapes, patterns, etc., seen within the typical surgical environment. For example, the colors or patterns chosen for the highly visible features do not typically appear in nature. In some cases, the highly visible features can be detected by the naked eye, i.e., the features emit or reflect light in the visible spectrum (wavelengths from approximately 390 nm to approximately 700 nm). In other cases, the highly visible features can be detected when exposed to a particular light source, such as infrared light.

In other embodiments, silicone material or the like may be applied to the medical items to repel any fluid, such as blood, and prevent the highly visible features from being soaked with fluid that may obscure their visibility. Absorbent medical items, such as sponges, towels, pads, cotton balls, drapes and gauze, are difficult to detect once saturated with blood. As such, the systems and methods described herein are particularly advantageous when applied to absorbent medical items.

In further embodiments, an extra structure formed from foam, plastic, etc., is applied or coupled to the medical items to provide highly visible colors, patterns, labels, images, shapes, etc.

In yet other embodiments, the medical items include a light source that makes the medical items more visible. The light source may be combined with other highly visible colors (e.g., bright colors), patterns, labels, images, shapes, structures, and/or materials. The light source may emit a continuous light or a pulsed/strobe light. In some cases, the light source may be visible to the naked eye. In other cases, the light source may emit a light (e.g., an infrared light) that is only visible with a camera or viewer, so that the light source does not interfere with the surgical procedure.

In general, embodiments enhance the visibility of medical items without affecting their functionality. For example, silicone material may be selectively applied to a sponge or towel to repel any fluid, e.g., blood, from the highly visible features, e.g., areas of highly visible color, while allowing the rest of the sponge or towel to absorb fluid as required. In addition, it is understood that the embodiments are formed from any combination of materials that are non-toxic, non-abrasive, and safe/suitable for use during a surgical procedure.

FIG. 1 illustrates an example sponge/towel 10 that includes one or more layers of absorbent material 12, e.g., a gauze-like or open-mesh fabric, such as woven cotton, or a nonwoven material. Although the sponge/towel 10 shown in FIG. 1 and other example embodiments described herein may be generally rectangular, it understood that the medical items according to aspects of the present invention may have any desired shape, e.g., circular, square, ovoid, etc. In contrast to the conventional white or near-white sponge/towel 1 also shown in FIG. 1, the sponge/towel 10 has a highly visible colored surface 14. The colored surface 14 may have one or more bright colors. Some bright colors are provided, for example, by light having any subset of wavelengths between approximately 485 nm (blue-green) to approximately 590 nm (yellow-orange). The colored surface 14 allows a surgical team to locate the sponge/towel 10 more easily, because the sponge/towel 10 does not blend visibly against the features/parts of the human body or other aspects of the surgical environment. In some embodiments, the absorbent material 12 is dyed with the highly visible color to provide the colored surface 14. In other embodiments, the absorbent material 12 is coated or otherwise covered with a material having a highly visible color to provide the colored surface 14. In general, the highly visible colors may be applied to the absorbent material 12 utilizing any variety of processes, including, but not limited to, spraying, immersion, painting, roll coating, flow coating, etc. Furthermore, it is understood that different types of materials may employed to produce the highly visible colors.

Figure 2:
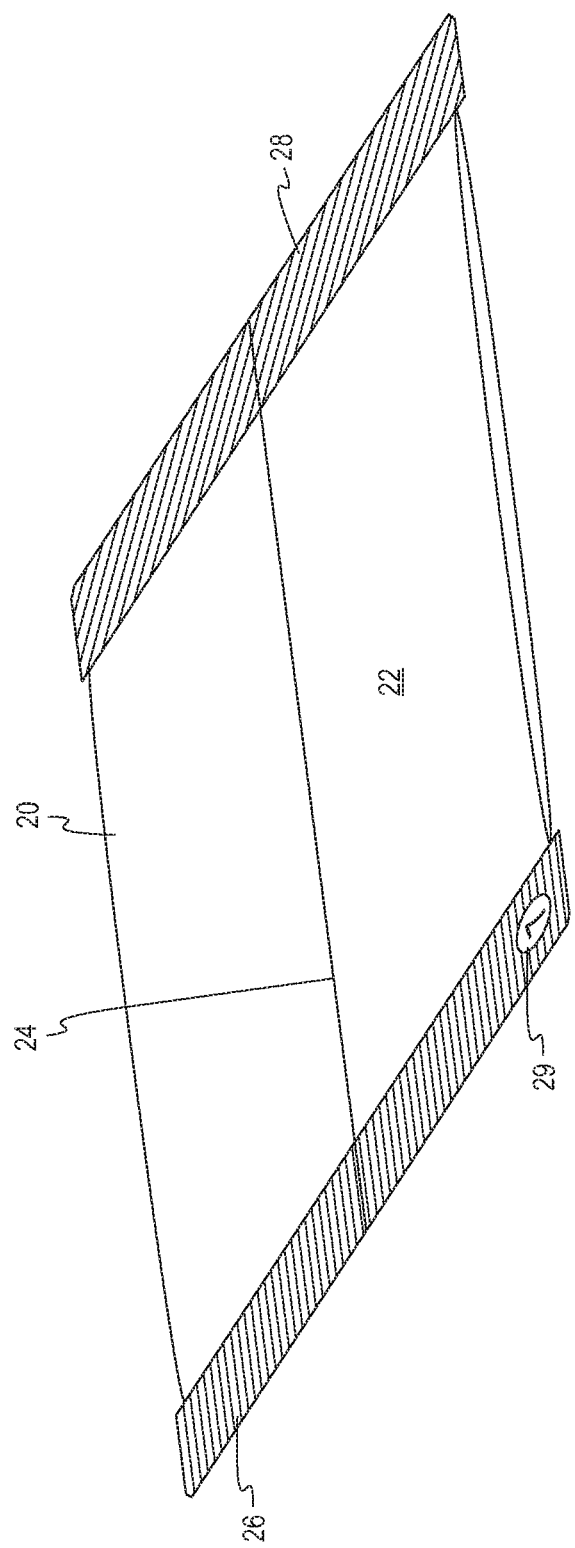
FIG. 2 illustrates an example sponge/towel with highly visible colored strips, according to aspects of the present invention.

FIG. 2 shows an example surgical sponge/towel 20 that includes one or more layers of absorbent material 22, e.g., a gauze-like or open-mesh fabric, such as woven cotton, or a nonwoven material. The sponge/towel 20 includes an elongated radio-opaque filament 24 disposed within the one or more layers of absorbent material 22. The filament 24 may be formed from a thermoplastic polymeric material containing a radio-opaque material, such as barium sulfate, so that the sponge/towel 20 can also be detected on an x-ray photograph if necessary. The sponge/towel 20 also includes two colored strips 26, 28, which may be secured to outer portions of the absorbent material 22, for example, by adhesive, stitching, or ultrasonic welding. The colored strips 26, 28 may, for example, be formed from material that is similar to sail cloth or medical tape. The colored strips 26, 28 are highly visible to the naked eye particularly during a surgical procedure. The colored strips 26, 28 may have bright colors that stand out particularly in contrast to the color of the absorbent material 22. The colored strips 26, 28 may be the same or different colors. For example, the strip 26 may be bright blue and the strip 28 may be bright green. Any one of the colored strips 26, 28 may also include a radio-opaque material, such as barium sulfate, such that it may be detected on an x-ray photograph.

The colored strips 26, 28 also include an outer surface that repels fluid, such as blood, and prevents the colored strips 26, 28 from being soaked with fluid that may obscure their visibility. For example, the colored strips 26, 28 may have an outer surface formed from silicone.

Silicones are inert, synthetic compounds. Silicones are polymers that include silicon together with carbon, hydrogen, oxygen, and sometimes other elements. Typically rubber-like, silicones exhibit many useful characteristics, including low thermal conductivity, low chemical reactivity, low toxicity, and thermal stability. Silicones can repel water and form watertight seals. They do not stick to many substrates. They do not support microbiological growth. In addition, they have high gas permeability. At room temperature (25° C.), the permeability of silicone for such gases as oxygen is approximately 400 times that of butyl rubber, making silicone useful for medical applications in which increased aeration is desired.

In other embodiments, the colored strips 26, 28 may not completely repel fluid, but at least reduces the effect that any absorbed fluid may have on the visibility of the colored strips 26, 28, e.g., allows the fluid to be spread over the entire area of the colored strips 26, 28. Although the colored strips 26, 28 may repel fluid, the absorbent material 22 retains its ability to absorb blood and other fluids during surgery. In other words, aspects of the present invention of not affect the function of the medical items whose visibility they enhance.

Additionally, any one of the colored strips 26, 28 may include a light-emitting material. As used herein, light-emitting materials refer to any combination of fluorescent, luminescent, photo-luminescent, and/or phosphorescent materials. For example, the colored strips 26, 28 may include strontium aluminate as a photo-luminescent material. Strontium aluminate is available as a solid odorless, nonflammable, pale yellow powder, heavier than water. It is chemically and biologically inert. Strontium aluminate produces visible light in a narrow band of wavelengths, thereby limiting the number of colors that can readily be produced. Combining pigment with the strontium aluminate allows the photo-luminescent material to excite the pigment. As such, the combination produces light in a wavelength that does not correspond to the wavelength of the strontium aluminate, and instead produces light in a color closer to that of the pigment. The strontium aluminate and the pigment are held in suspension in a carrier. In one embodiment, the carrier is a plastisol, or a suspension of PVC particles in a plasticizer. Holding the mixture of the strontium aluminate and the pigment in the carrier allows for an even mixture of the components. The photo-luminescent material may be held in the carrier at a ratio from about 10% to about 60% strontium aluminate by weight with the balance being pigment and plastisol. This mixture can be applied to the colored strips 26, 28.

When activated with a suitable dopant (e.g. europium (labeled SrAl2O4:Eu)), it acts as a photo-luminescent phosphor with long persistence of phosphorescence. This material may be mixed into silicone to provide a visible product under bright light, day conditions. While phosphorescent materials may also be light reflectors, they also act as a source of light. Phosphorescent materials typically operate by absorbing a range of radiation wavelengths, converting this radiation to radiation in the visible spectrum and emitting it as light, visible to the eye. Phosphorescent materials are those materials that are capable of producing radiation in the visible spectrum for a period of time after the initial absorption of radiation has stopped. In other embodiments, the colored strips 26, 28 may include such phosphorescent materials.

Any portion of the sponge/towel 20 may include a light-emitting material. As shown in FIG. 2, a light-emitting material 29 is provided along the colored strip 26, e.g., as an ornamental design or image, to makes the sponge/towel 20 further visible. The light-emitting material 29 may be coated or otherwise applied to the colored strip 26. Alternatively, the light-emitting material 29 may be attached as a separate structure to the colored strip 26. In some embodiments, the colored strips 26, 28 may include photo-luminescent materials that emit infrared light.

It should be further understood that the descriptions of the light emitting materials and the structure of the surgical sponges and towels are presented as examples only, and that a wide variety of materials may be used to produce the desired light-emitting characteristics that enhance the visibility of the medical items, e.g. the sponge/towel 10.

Furthermore, any one of the colored strips 26, 28 may include a highly reflective material, such as a metallic material, that effectively reflects light to make the sponge/towel more visible.

Figure 3:
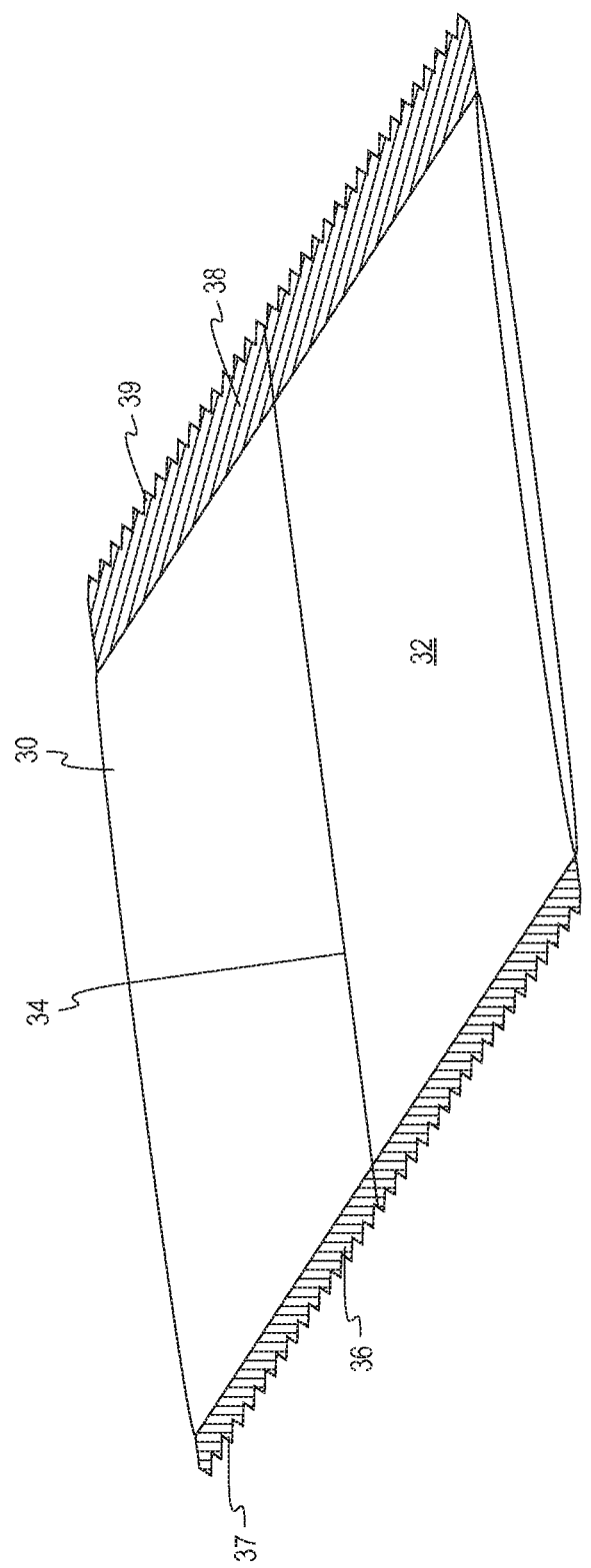
FIG. 3 illustrates an example sponge/towel with highly visible colored strips with distinguishable structural features, according to aspects of the present invention.

FIG. 3 shows an example sponge/towel 30 with highly visible structural features. Like the sponges/towels above, the sponge/towel 30 includes one or more layers of absorbent material 32 as well as an elongated radio-opaque filament 34 that can be seen in an x-ray photograph. The sponge/towel 30 also includes colored strips 36, 38 with highly visible teeth 37, 39, respectively. To define opposing edges of the sponge/towel 30, the colored strips 36, 38 may be secured to the absorbent material 32, for example, by adhesive, stitching, or ultrasonic welding. The colored strips 36, 38 may, for example, be formed from material that is similar to sail cloth or medical tape. The colored strips 36, 38 may have bright light colors that stand out particularly from the color of the absorbent material 32. In addition, the colored strips 36, 38 may include an outer surface that repels fluid, such as blood, and prevents the colored strips 36, 38 from being soaked with the fluid which may obscure their visibility. As shown in FIG. 3, the teeth 37, 39 may be defined, for example, by pointed triangles cut at approximately 90-degrees. In combination with the color of the strips 36, 38, the respective teeth 37, 39 provide a distinctive shape that makes the sponge/towel 30 more visible. The shape shown in FIG. 3 is provided as an example; it is understood that other shapes, e.g., other jagged edges, non-jagged edges, curves, etc., may be implemented.

Figure 4:
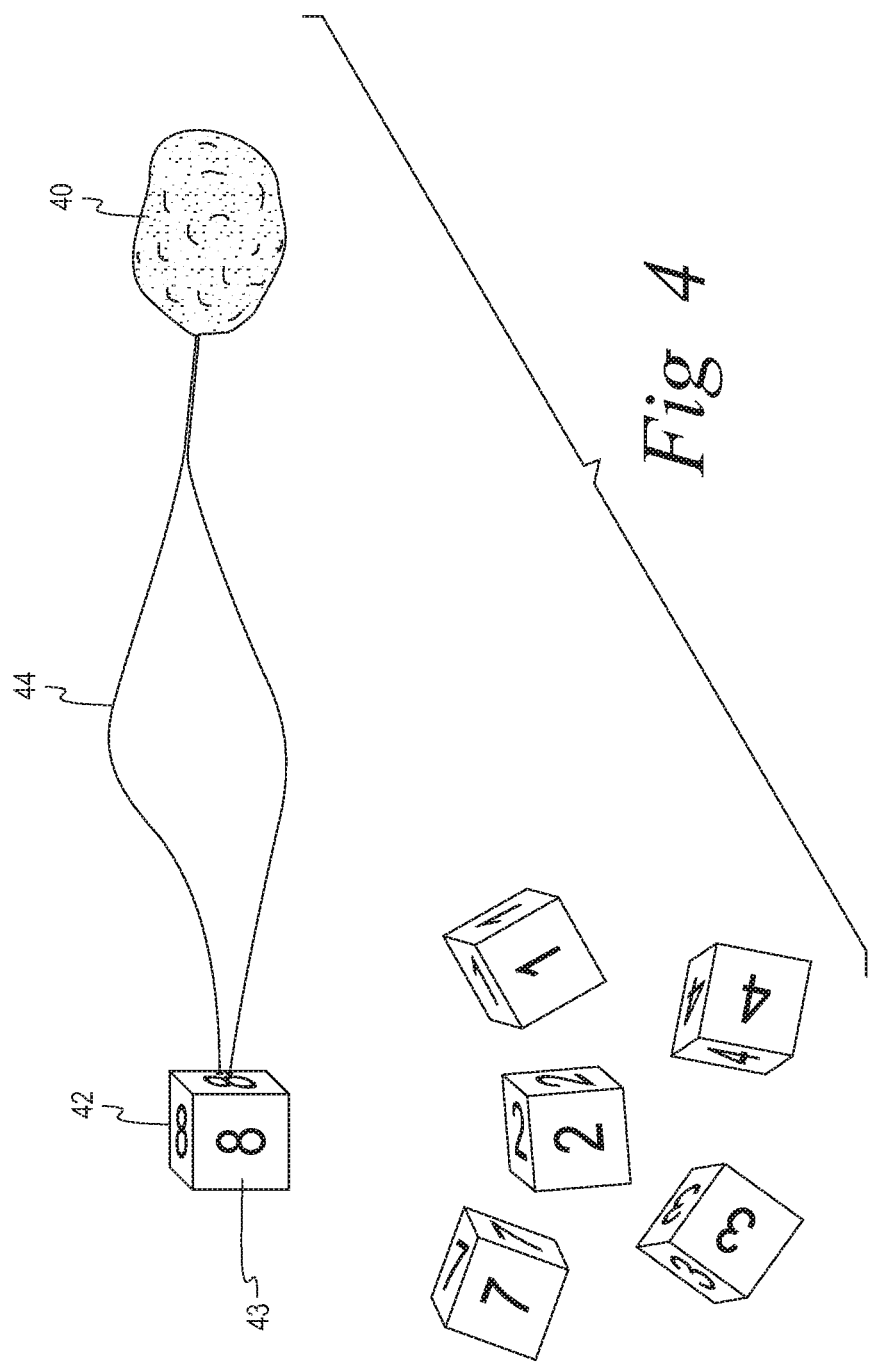
FIG. 4 illustrates an example sponge/towel coupled to highly visible beads with a tether, according to aspects of the present invention.

FIG. 4 shows an example surgical sponge/towel 40 with a structure to enhance its visibility. In particular, the surgical sponge/towel 40 includes a bead 42 with an identifying label 43. The bead 42 may be coupled securely to the sponge/towel 40 by sewing, crimping, riveting, gluing, or other type of fastening. For example, the bead 42 may be coupled to the sponge/towel 20 shown in FIG. 2 in place of the light-emitting material 29. Alternatively, the bead 42 may be placed on a tether 44 coupled securely to the sponge/towel 40. The tether 44 may be formed from a highly visible material (e.g., bright colors, highly reflective material, light-emitting coating, etc.). The label 43 provides a number that uniquely identifies the sponge/towel 40. For example, the sponge/towel 40 may be a member of a set of sponges/towels that are labeled with numbers in a particular range. The label 43 may be visibly shown from each face of the bead 42. The label 43 facilitates in the accounting of medical items during surgery. If a set of sponges/towels labeled with numbers in a particular range, e.g., 1 to 20, are employed during surgery, the surgical team can easily determine that one of the sponges/towels is missing if a sponge/towel with a number in the range, e.g. 8, is not present at the time of accounting. In addition to providing identifying labels, the beads can have a variety of other highly visible characteristics, e.g., bright colors, highly reflective material, light-emitting coating, etc. The bead 43 may be formed from a material, such as acrylic, which repels fluid and ensures that the bead 43 remains highly visible. Furthermore, the sponge/towel 40 can have other highly visible characteristics, such as colored strips as described above.

Figure 5:
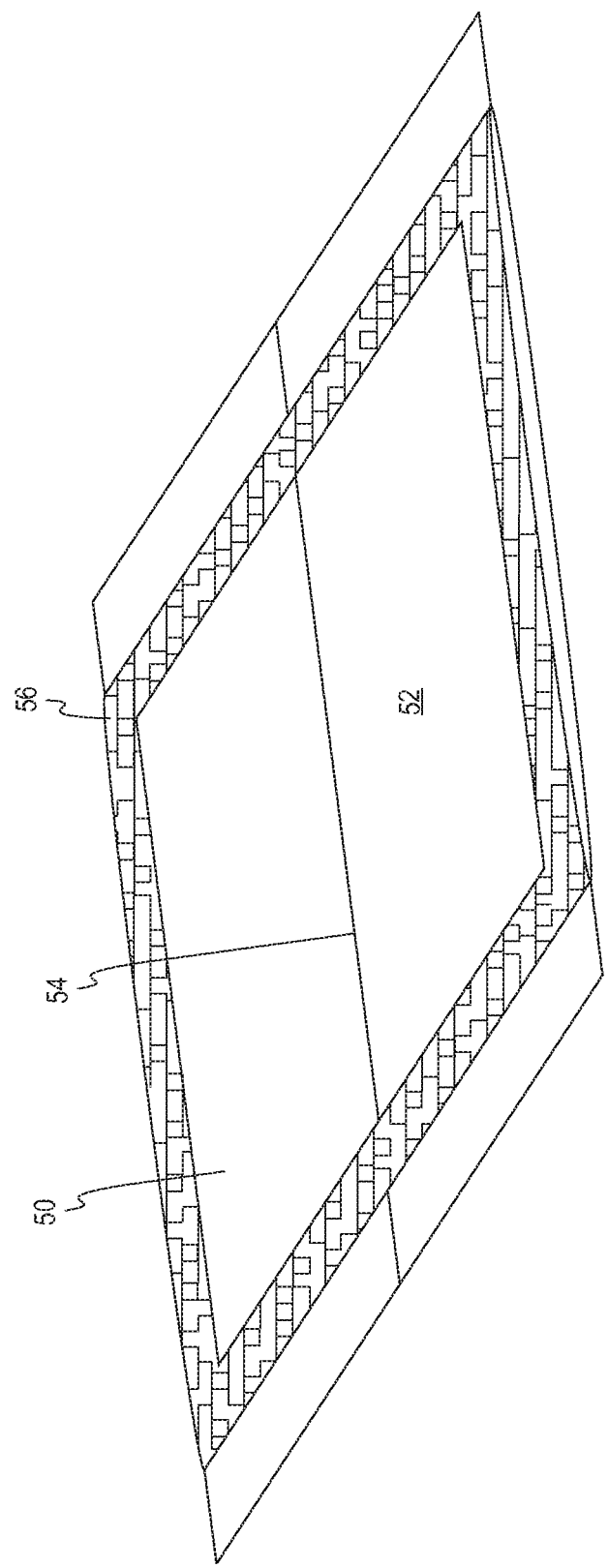
FIG. 5 illustrates an example sponge/towel with a highly visible a foam-based structure disposed along the periphery of the sponge/towel, according to aspects of the present invention.

FIG. 5 illustrates an example sponge/towel 50 coupled to a foam-based structure 56 that makes the sponge/towel 50 highly visible. Like the sponges/towels above, the sponge/towel 50 includes one or more layers of absorbent material 52 as well as an elongated radio-opaque filament 54 that can be seen in an x-ray photograph. The foam-based structure 56 may be coupled to the sponge/towel 50 according to any technique, including, but not limited to, adhesive bonding, sewing, mechanical fastening, or thermal bonding. The foam-based structure 56 may be formed from quantum foam, polyurethane foam (foam rubber), extruded polystyrene (XPS) foam, polystyrene, phenolic foam, or any other similarly suitable foam. As shown in FIG. 5, the foam-based structure 56 fits around the periphery of and frames the sponge/towel 50 at its outer edges. The foam-based structure 56 may have bright colors, highly reflective material, light-emitting coating, etc., that stand out particularly from the color of the absorbent material 56.

Figure 6:
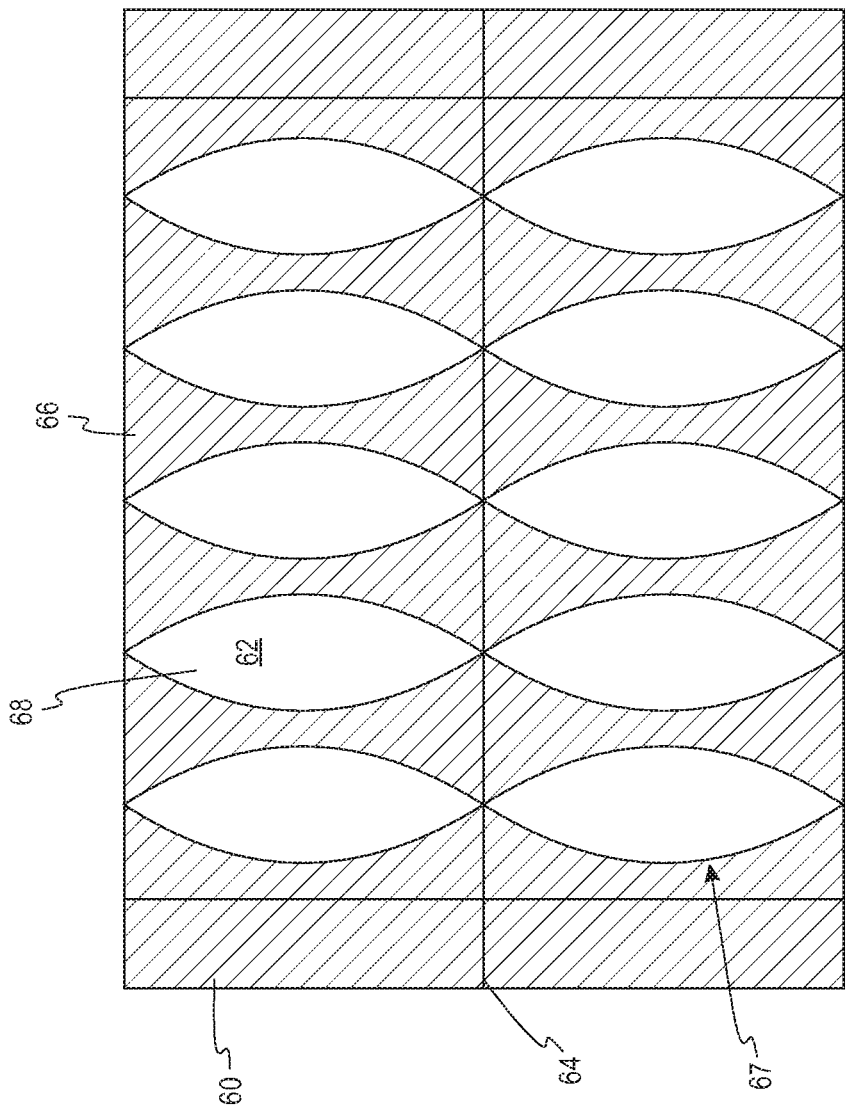
FIG. 6 illustrates an example sponge/towel with a silicone (or similar) material applied to the outer surface of the sponge/towel in a visually distinctive pattern, according to aspects of the present invention.

FIG. 6 illustrates an example sponge/towel 60 with a silicone (or similar) material 66 applied to its outer surface according to a visually distinctive pattern 67. Like the sponges/towels above, the sponge/towel 60 includes one or more layers of absorbent material 62 as well as an elongated radio-opaque filament 64 that can be seen in an x-ray photograph. The silicone material 66 is applied to the outer surface of the sponge/towel 60 with a striped pattern 67. The striped pattern 67 provides openings to allow fluid, such as blood, to be absorbed by the absorbent material 62. The silicone 66 may be colored so that the striped pattern 67 may include a highly visible color. Accordingly, the striped pattern 67 is visually distinctive and makes the sponge/towel 60 easier to identify during surgery. In addition, the silicone advantageously repels fluid and ensures that the striped pattern 67 remains highly visible. In alternative embodiments, rather than bonding the silicone 66 to the absorbent material 62, the silicone 66 may form an enclosure into which the absorbent material 62 can be placed.

Figure 7:
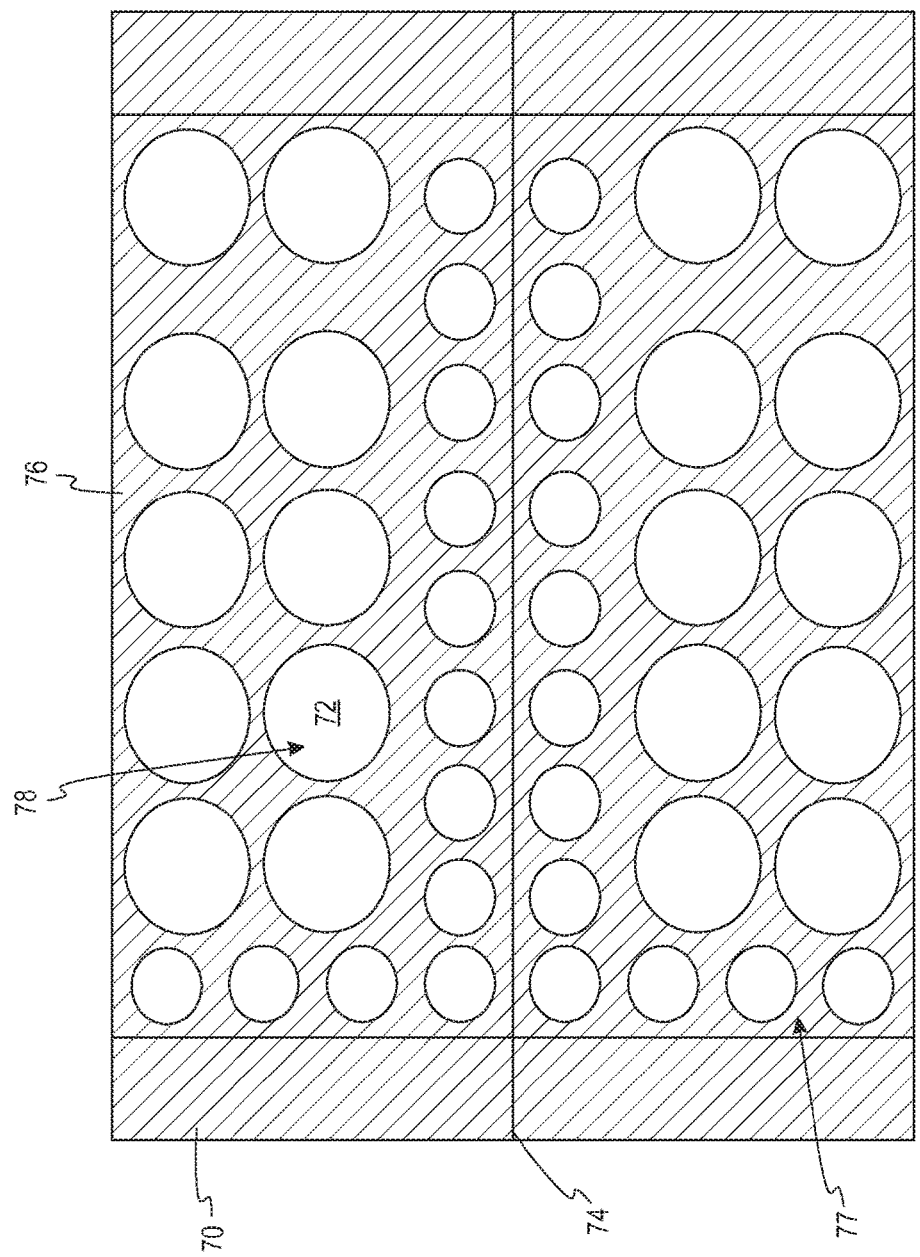
FIG. 7 illustrates an example sponge/towel with a silicone (or similar) material applied to the outer surface of the sponge/towel in another visually distinctive pattern, according to aspects of the present invention.

FIG. 7 illustrates an example sponge/towel 70 with a silicone material (or similar material) 76 applied to its outer surface according to another visually distinctive pattern 77. The sponge/towel 70 includes an elongated radio-opaque filament 74. Although the sponge/towel 70 is similar to the sponge/towel 60 in FIG. 5, the silicone material 76 defines a pattern 77 with circular openings 78. The circular openings 78 to allow fluid, such as blood, to be absorbed by the absorbent material 72. The silicone 76 may be colored so that the areas around the circular openings 78 may have a highly visible color. Accordingly, the pattern 77 is visually distinctive and makes the sponge/towel 70 easier to identify during surgery. In addition, the silicone advantageously repels fluid and ensures that the pattern 77 remains highly visible. In alternative embodiments, rather than bonding the silicone 76 to the absorbent material 72, the silicone 76 may form an enclosure into which the absorbent material 72 can be placed.

Figure 8:
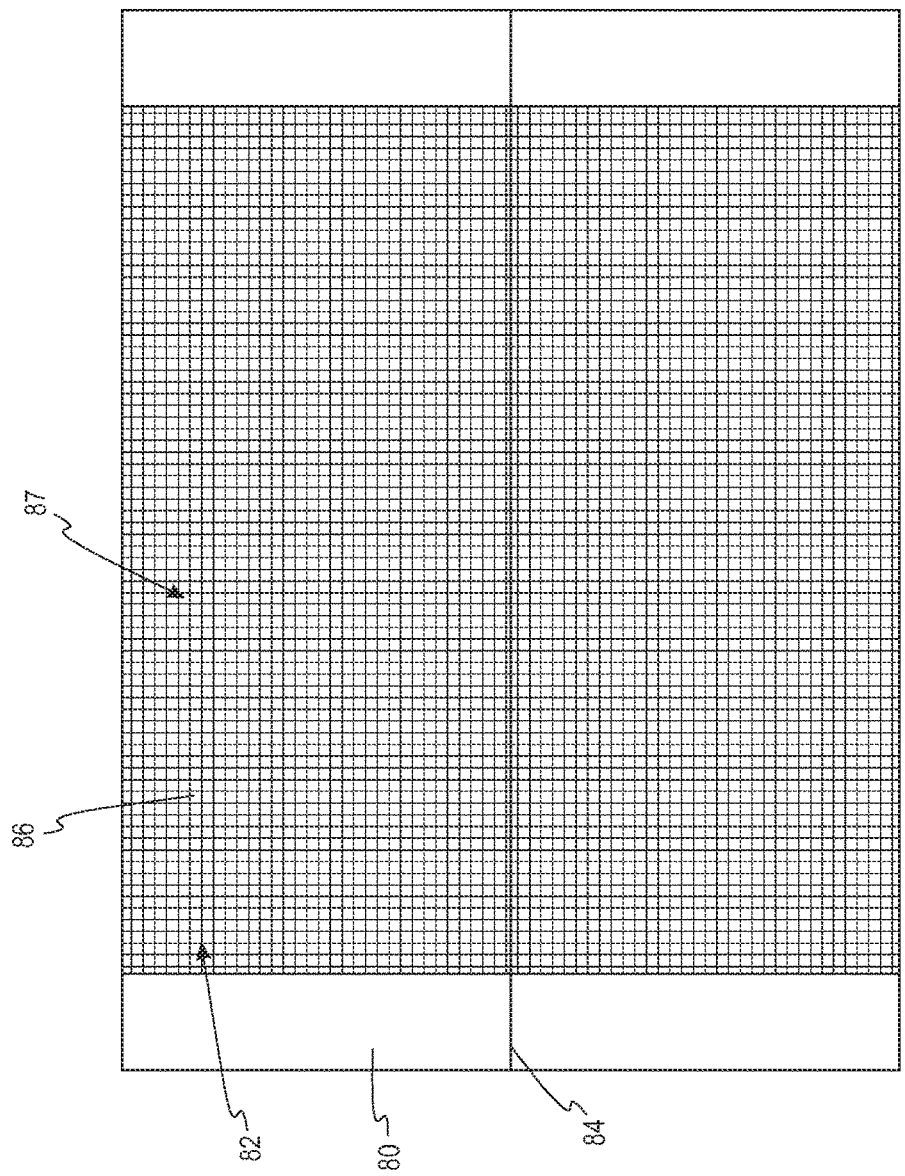
FIG. 8 illustrates an example sponge/towel enclosed in a highly visible plastic mesh, according to aspects of the present invention

FIG. 8 illustrates an example sponge/towel 80 with a mesh 86. Like the sponges/towels above, the sponge/towel 80 includes one or more layers of absorbent material 82 as well as an elongated radio-opaque filament 84 that can be seen in an x-ray photograph. A thin (e.g., approximately 0.5 mm to approximately 1 mm) plastic mesh material 86 encloses the sponge/towel 80. The mesh 86 may be formed from synthetic or semi-synthetic organic solids that are moldable. For example, the mesh 86 may be formed from plastic. Mesh openings 87 in the mesh 86 allow fluid, such as blood, to be absorbed by the absorbent material 82. The plastic forming the mesh 86 may be colored so that the mesh 86 may have a highly visible color. Accordingly, the sponge/towel 80 is easier to identify during surgery. In addition, the plastic advantageously repels fluid and ensures that the mesh 86 remains highly visible.

Figure 9:
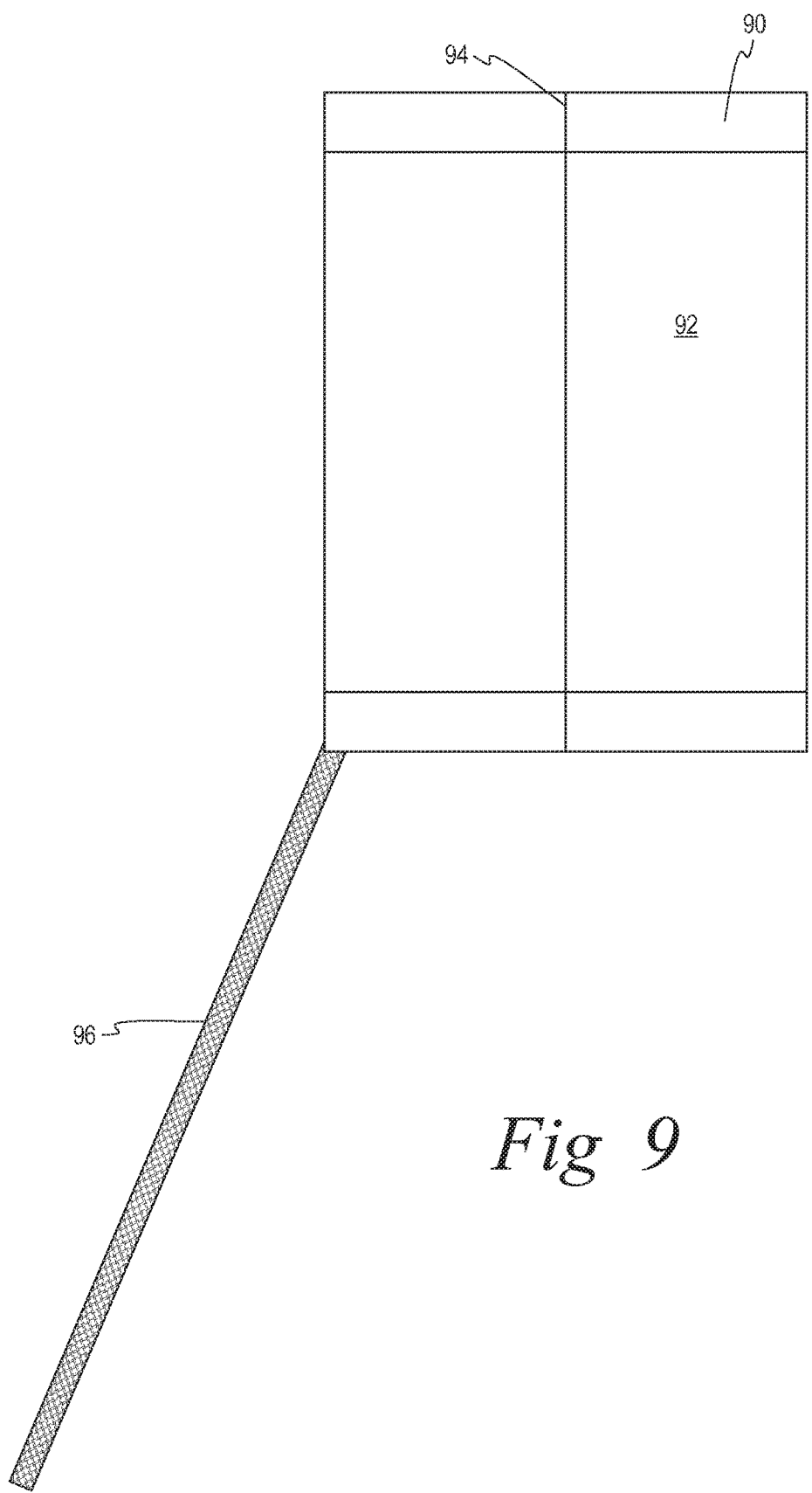
FIG. 9 is an example sponge/towel with a highly visible tether, according to aspects of the present invention.

FIG. 9 illustrates an example sponge/towel 90 with a tether 96. Like the sponges/towels above, the sponge/towel 90 includes one or more layers of absorbent material 92 as well as an elongated radio-opaque filament 94 that can be seen in an x-ray photograph. The tether 96 is coupled to the absorbent material 92 to make it more visible and easily retrievable. The tether 96 is formed from a thin (e.g., approximately 0.5 mm to approximately 1 mm) plastic mesh material. The plastic forming the tether 96 may be colored so that the tether 96 has a highly visible color. Accordingly, the sponge/towel 90 is easier to identify during surgery. In addition, the plastic advantageously repels fluid and ensures that the tether 96 remains highly visible.

Figure 10:
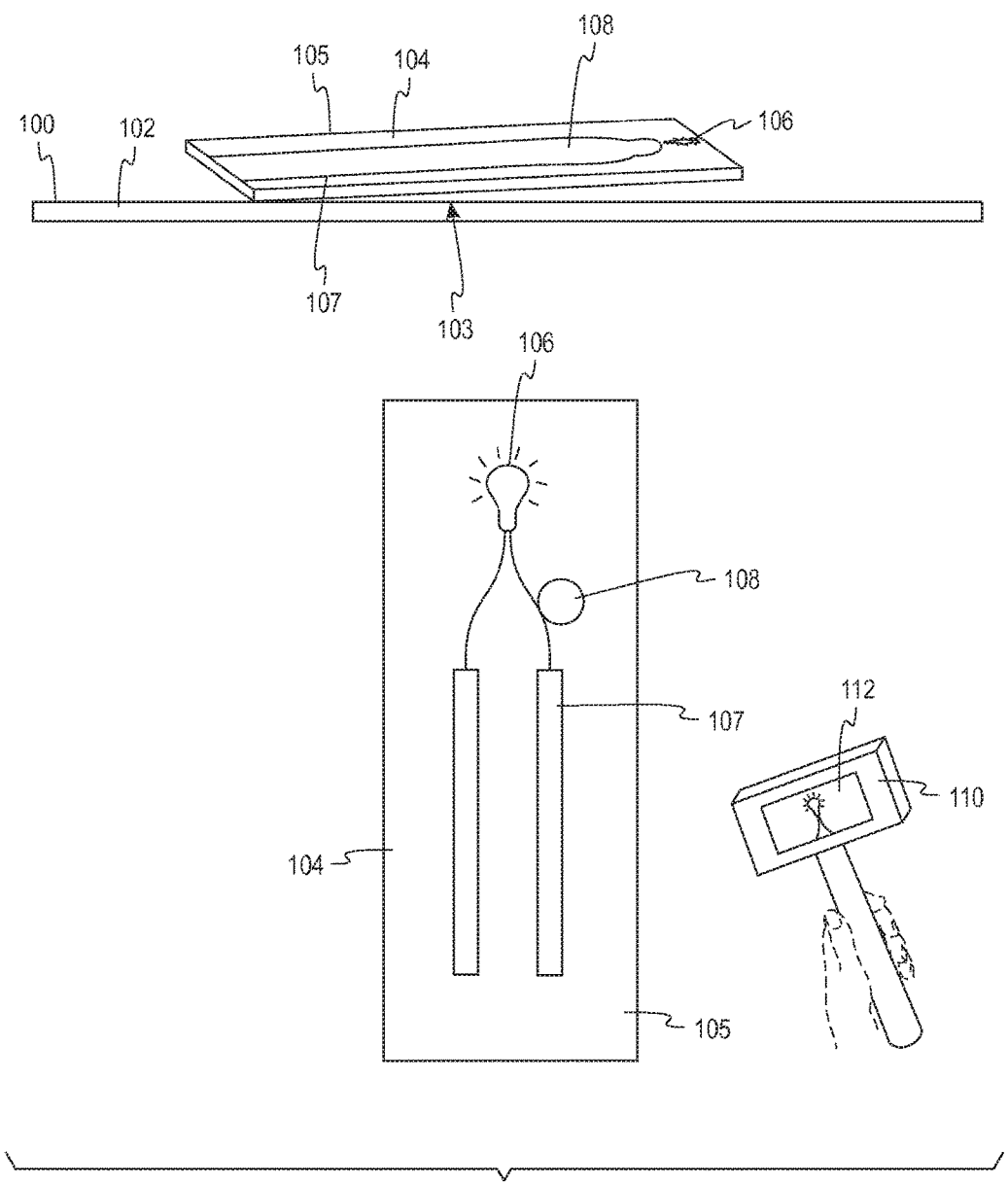
FIG. 10 illustrates an example sponge/towel with a light device that makes the sponge/towel easy to locate, according to aspects of the present invention.
Figure 11:
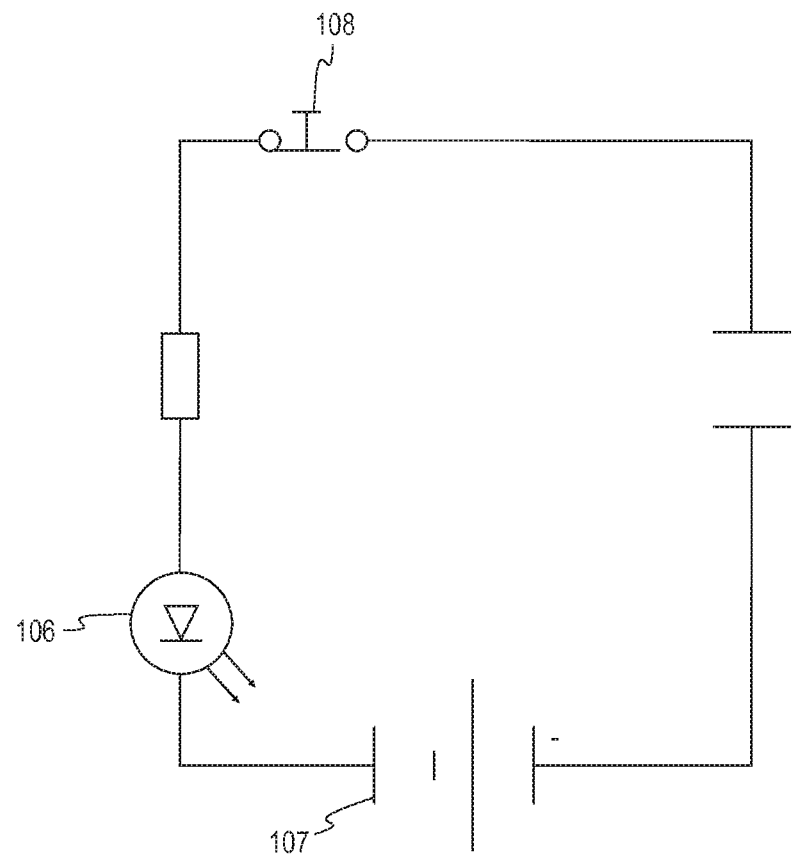
FIG. 11 illustrates a circuit diagram of the light device of FIG. 10.

FIG. 10 illustrates an example sponge/towel 100 with a light device 104. Like the sponges/towels above, the sponge/towel 100 includes one or more layers of absorbent material 102. The light device 104 includes a water-tight housing 105 that contains a light source 106 and a power source 107 (e.g., a lithium battery cell). The light source 106 is operated/activated by a switch 108. The light device 104 is coupled to the absorbent material 102 according to any suitable technique 103 (e.g., sewing, adhesive, mechanical fastener, hook and loop fastener, etc.). The light source 106 is activated before it is introduced into the surgical environment, thereby making the sponge/towel 100 more visible and easier to identify during surgery. FIG. 11 illustrates an electrical circuit diagram for the light device 104.

In some embodiments, the light source 106 emits an infrared light, rather than visible light which may interfere with the ability to conduct the surgical procedure. As such, an infrared camera/viewer 110 as shown in FIG. 10 may be required to see the light source 106 and locate the sponge/towel 100 through a display 112. Accordingly, before the surgical team begins closure, the surgical team scans the surgical field with the infrared camera/viewer 110. Infrared light is electromagnetic radiation with longer wavelengths than those of visible light, extending from the nominal red edge of the visible spectrum at 700 nanometers (nm) to 1 mm. This range of wavelengths corresponds to a frequency range of approximately 430 THz down to 300 GHz.

In further embodiments, the light source 106 may emit a pulsed light, e.g., with an interval setting of 0.5 seconds ON and 1 second OFF. As such, the light device 104 may provide an infrared strobe/beacon that is highly visible through the camera/viewer 110.

The infrared camera/viewer 110 may use an infrared sensor operating at ambient temperature, or a sensor stabilized at a temperature close to ambient using small temperature control elements. Modern uncooled infrared detectors use sensors that work by the change of resistance, voltage or current when heated by infrared radiation. These changes are then measured and compared to the values at the operating temperature of the sensor. Uncooled infrared sensors can be stabilized to an operating temperature to reduce image noise, but they are not cooled to low temperatures and do not require bulky, expensive cryogenic coolers. This makes infrared cameras/viewers smaller and less costly. Active infrared vision combines infrared illumination of spectral range 1 nm-1 mm (just below the visible spectrum of the human eye) with cameras sensitive to this light. The resulting scene, which is dark to a human observer, appears as an image on a display device. Because active infrared vision systems can incorporate illuminators that produce high levels of infrared light, the resulting images are typically higher resolution than other night vision technologies.

In addition to sponges/towels, it is understood that aspects of the present invention can be employed with other types of medical items, including, but not limited to, instruments, tools, knives, scalpels, other hardware, containers, etc. For example, a photo-luminescent material (e.g., emitting light with visible and/or infrared wavelengths) may be applied to these other medical items. In an example application, a photo-luminescent material emitting light with infrared wavelengths may be applied to a bandage used in battlefield medicine, where the bandage can be easily identified by an appropriate viewer but may be camouflaged and less detectable to the naked eye, particularly of opposing soldiers.

Figure 12:
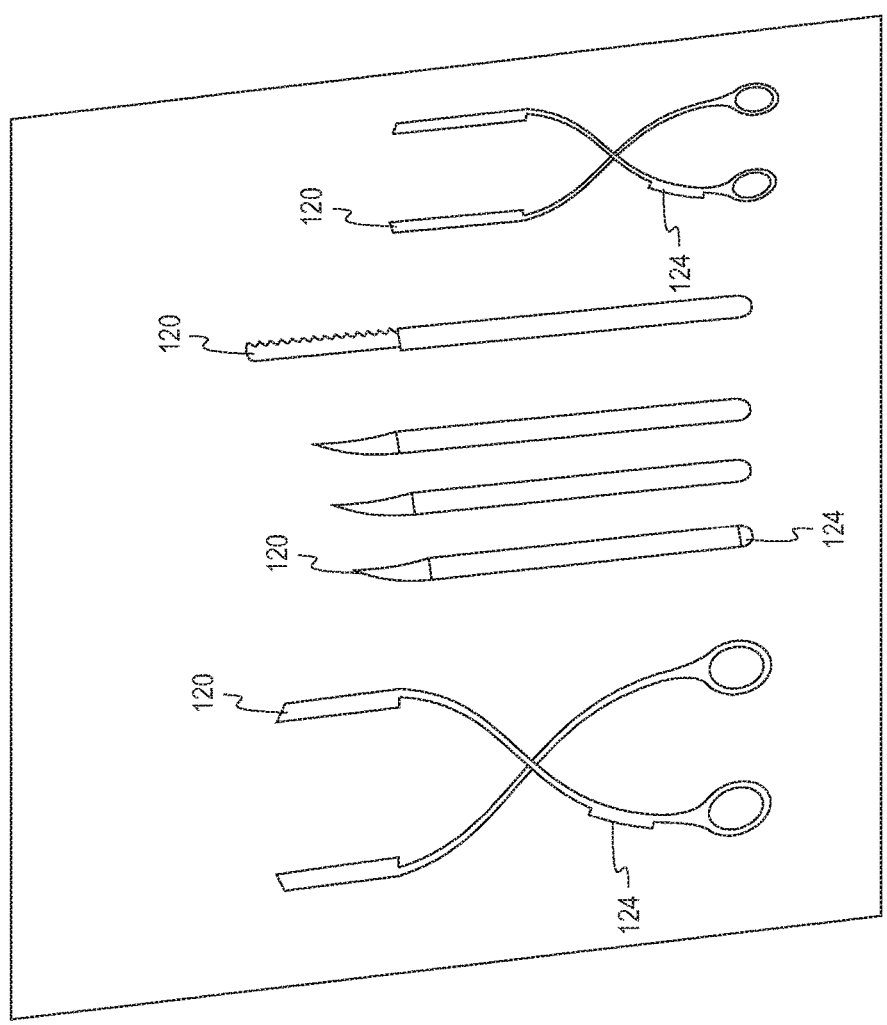
FIG. 12 illustrates other example medical items, each with a light device that makes the medical item easy to locate, according to aspects of the present invention.

As shown in FIG. 12, for example, other example medical items 120, such as forceps, scalpels, knives, etc., are combined with light devices 124. Like the light device 104 described above, the light devices 124 include a liquid-tight housing that contains a light source and a power source and are operated/activated by a switch. The light devices 124 are coupled to the medical items 120 according to any suitable technique (e.g., sewing, adhesive, mechanical fastener, hook and loop fastener, etc.). The light sources 124 make the medical items 120 more visible and easier to identify during surgery.

Figure 13:
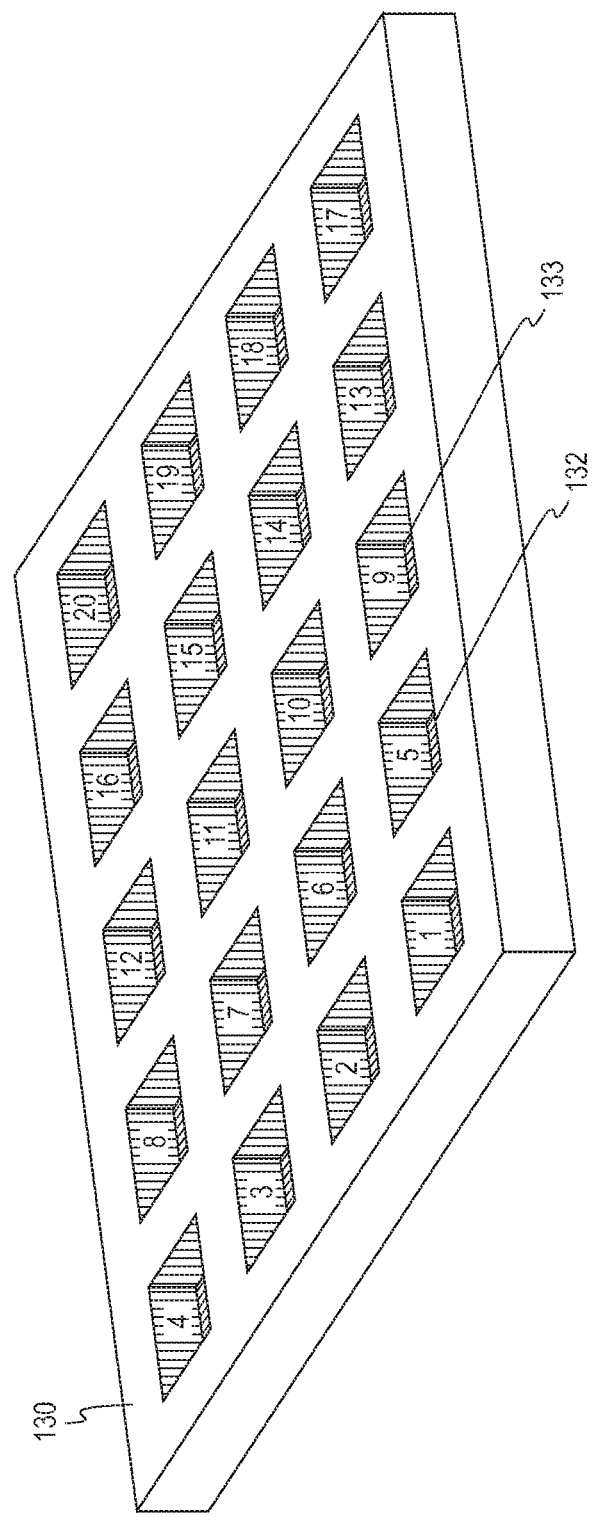
FIG. 13 illustrates an example tray for storing and tracking medical items, according to aspects of the present invention.

In addition to employing the systems and methods above to make individual surgical instruments more visible, FIG. 13 illustrates an example tray 130 that helps the surgical team to account for medical items before the patient is closed. The tray 130 receives individual medical items, e.g., sponges or towels, into respective receptacles 132, which may be recesses that keep the medical items in place. Each receptacle 132 is colored, e.g., with a fluorescent color, and is labeled with a number 133. The color of the receptacle 132 allows the surgical team to determine more easily that a medical item is disposed in the receptacle 132, particularly after the medical item has been used and is possibly soaked with blood and fluid. Furthermore, the numbers 133 in the receptacles 132 facilitate counting of the medical items. In addition to providing an approach that collects and accounts for surgical instruments after a surgical procedure, the tray 130 may also be used to organize medical items before the surgical procedure. In some embodiments, the numbers 133 (or other labels) may correspond uniquely with respective numbers (or labels) that have been assigned and attached to the medical items, as described above.

To illustrate the advantages of the systems and methods disclosed herein, a laparoscopic gall bladder surgery (cholecystectomy) is described. This surgical procedure removes the gallbladder and gallstones through several small incisions in the abdomen. This surgical procedure typically lasts for approximately one hour, from first incision to wound closure. Pre- and post-operative preparations generally require an additional one-hour. Thus, the patient/insurance company is typically charged for approximately two hours of surgery time.

However, if the surgical team cannot locate one of the surgical sponges used in the procedure, the surgical team must search the surgical field, supply tables, surrounding floor, etc. According to conventional protocols, a portable x-ray is employed if the surgical team cannot locate the sponge after a thorough search. The patient is kept under general anesthesia on the operating table until the x-ray is taken, processed, and interpreted. If no evidence of the sponge is located in the x-ray photograph, it is presumed that the sponge was misplaced outside the patient, and the patient is transferred from the operating room. If the sponge is located in the x-ray photograph, the patient is re-examined, or re-opened, to search for the sponge. The initial search may last approximately 15 to 20 minutes, with the x-ray adding at least another 30 minutes, for a total of 45-50 minutes of additional anesthesia and patient time in the operating room. Therefore, the anesthesia exposure time and corresponding risks increase, as does the time-based charges for anesthesia care and operating room time.

If the gall bladder surgery, however, is performed, for example, with a colored sponge with an infrared light device described above, a missing sponge can be efficiently and rapidly. At most, an infrared camera/viewer is required to examine the surgical area. The infrared signal from the light device makes the missing sponge highly visible in any operating room environment. By using this system, the search for the missing sponge can be reduced to less than one minute, resulting in considerable savings and less risk associated with extended exposure to anesthesia.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A medical item, comprising:
an absorbent material having a shape with a pair of opposing edges, the absorbent material being adapted to absorb fluid during a medical procedure, the absorbent material having an outer surface that reflects one or more first wavelengths of light to provide the absorbent material one or more first colors; and
a pair of separate and distinct strips of enhancing material, a first of the pair of separate and distinct strips being directly secured to a first of the pair of opposing edges of the absorbent material and a second of the pair of separate and distinct strips being directly secured to a second of the pair of opposing edges of the absorbent material, the pair of separate and distinct strips of enhancing material reflecting or emitting one or more second wavelengths to provide the pair of separate and distinct strips of enhancing material with one or more second colors, the one or more second wavelengths being between approximately 485 nm to approximately 590 nm and being different from the one or more first wavelengths of the absorbent material, the pair of separate and distinct strips of enhancing material including silicone and being configured to repel the fluid such that the pair of separate and distinct strips of enhancing material continues to reflect or emit the one or more second colors when the pair of separate and distinct strips of enhancing material is exposed to the fluid.

2. The medical item of claim 1, wherein the one or more enhancing materials include a fluorescent, luminescent, photo-luminescent, or phosphorescent material.

3. The medical item of claim 1, wherein the one or more enhancing materials include a reflective metallic material.

4. The medical item of claim 1, further comprising an enhancing device coupled to the absorbent material, the enhancing device reflecting or emitting one or more third wavelengths, the one or more third wavelengths being different from the one or more first wavelengths of the absorbent material, the enhancing device including a light device having a liquid-tight housing, the liquid-tight housing including therein a light source emitting the one or more third wavelengths, a battery, and a switch electrically coupled together in a circuit, the switch being selectively operable to (i) deliver power from the battery to the light source and (ii) activate the light source to emit the one or more third wavelengths.

5. The medical item of claim 4, wherein the light device emits pulsed light.

6. The medical item of claim 4, wherein the one or more third wavelengths are not in the visible spectrum and can only be seen through a camera or viewer.

7. The medical item of claim 6, wherein the one or more third wavelengths provide infrared light.

8. The medical item of claim 1, further comprising a bead with a label uniquely assigned to the medical item.

9. The medical item of claim 1, further comprising a tether that extends from the absorbent material.

10. The medical item of claim 1, wherein each of the pair of separate and distinct strips of enhancing material has an outermost edge that has a non-linear shape.

11. The medical item of claim 10, wherein the non-linear shape aids in making the medical item visible during use in a patient during a surgical procedure.

12. The medical item of claim 10, wherein the non-linear shape includes a plurality of teeth.

13. The medical item of claim 12, wherein each of the plurality of teeth is a non-jagged tooth.

14. The medical item of claim 1, wherein the first of the pair of separate and distinct strips is directly secured to the first of the pair of opposing edges of the absorbent material via stitching and the second of the pair of separate and distinct strips is directly secured to the second of the pair of opposing edges of the absorbent material via stitching.

15. The medical item of claim 1, further comprising a layer of colored silicone applied to the absorbent material between the pair of separate and distinct strips of enhancing material, the layer of colored silicone having a pattern with a first plurality of openings through which the fluid can pass to be absorbed by the absorbent material and a second plurality of openings through which the fluid can pass to be absorbed by the absorbent material, the first plurality of openings having a first size and the second plurality of openings having a second size that is different from the first size.

16. The medical item of claim 15, wherein each of the first plurality of openings is a generally circular opening and each of the second plurality of openings is a generally circular opening.

* * * * *